US008170832B2

(12) United States Patent
Young et al.

(10) Patent No.: US 8,170,832 B2
(45) Date of Patent: May 1, 2012

(54) MEASUREMENT AND ENDPOINTING OF SAMPLE THICKNESS

(75) Inventors: Richard J. Young, Beaverton, OR (US); Brennan Peterson, Portland, OR (US); Rudolf Johannes Peter Gerardus Schampers, Belfeld (NL); Michael Moriarty, Portland, OR (US)

(73) Assignee: FEI Company, Hillsboro, OR (US)

( * ) Notice: Subject to any disclaimer, the term of this patent is extended or adjusted under 35 U.S.C. 154(b) by 119 days.

(21) Appl. No.: 12/611,023

(22) Filed: Nov. 2, 2009

(65) Prior Publication Data

US 2010/0116977 A1  May 13, 2010

Related U.S. Application Data

(60) Provisional application No. 61/110,394, filed on Oct. 31, 2008.

(51) Int. Cl.
*G01N 23/04* (2006.01)
*G06F 17/00* (2006.01)

(52) U.S. Cl. .......... 702/170; 702/97; 702/172; 702/155; 850/8

(58) Field of Classification Search .................. 702/170, 702/97, 155, 172
See application file for complete search history.

(56) References Cited

U.S. PATENT DOCUMENTS

| 4,629,898 | A | 12/1986 | Orloff et al. |
|---|---|---|---|
| 5,093,572 | A | 3/1992 | Hosono |
| 5,525,806 | A | 6/1996 | Iwasaki et al. |
| 6,276,987 | B1 | 8/2001 | Li et al. |
| 6,589,709 | B1 | 7/2003 | Okoroanyanwu et al. |
| 6,630,288 | B2 | 10/2003 | Shields et al. |
| 6,653,231 | B2 | 11/2003 | Okoroanyanwu et al. |
| 6,683,316 | B2 | 1/2004 | Schamber et al. |
| 6,716,571 | B2 | 4/2004 | Gabriel et al. |
| 6,774,365 | B2 | 8/2004 | Okoroanyanwu et al. |
| 6,815,359 | B2 | 11/2004 | Gabriel et al. |
| 6,828,259 | B2 | 12/2004 | Fisher et al. |
| 6,905,623 | B2 | 6/2005 | Lundquist et al. |
| 6,914,244 | B2 * | 7/2005 | Alani ............................ 250/307 |
| 7,053,372 | B2 | 5/2006 | Park et al. |

(Continued)

FOREIGN PATENT DOCUMENTS

EP    2149897    2/2010

(Continued)

OTHER PUBLICATIONS

Aden, Gary, et al., 'Addendum to Proceedings of Modern Microscopy/Scanning 2003,' May 3-5, 2003, pp. 157-161.

(Continued)

*Primary Examiner* — Hal Wachsman
(74) *Attorney, Agent, or Firm* — Scheinberg & Griner, LLP; Michael O. Scheinberg; David Griner (57) ABSTRACT

A method for Transmission Electron Microscopy (TEM) sample creation. The use of a Scanning Electron Microscope (SEM)—Scanning Transmission Electron Microscope (STEM) detector in the dual-beam focused ion beam (FIB)/SEM allows a sample to be thinned using the FIB, while the STEM signal is used to monitor sample thickness. A preferred embodiment of the present invention can measure the thickness of or create TEM samples by using a precise endpoint detection method. Preferred embodiments also enable automatic endpointing during TEM lamella creation and provide users with direct feedback on sample thickness during manual thinning. Preferred embodiments of the present invention thus provide methods for endpointing sample thinning and methods to partially or fully automate endpointing.

30 Claims, 8 Drawing Sheets

U.S. PATENT DOCUMENTS

| | | | |
|---|---|---|---|
| 7,141,791 | B2 | 11/2006 | Masnaghetti et al. |
| 7,355,177 | B2 | 4/2008 | Kamiya et al. |
| 7,391,039 | B2 | 6/2008 | Kitamura et al. |
| 2003/0025087 | A1 | 2/2003 | Schamber et al. |
| 2004/0129880 | A1 | 7/2004 | Okoroanyanwu et al. |
| 2005/0184233 | A1 | 8/2005 | Park et al. |
| 2008/0258056 | A1* | 10/2008 | Zaykova-Feldman et al. ............... 250/307 |
| 2008/0296498 | A1* | 12/2008 | Hong ............... 250/311 |
| 2009/0242759 | A1* | 10/2009 | Bray et al. ............... 250/307 |
| 2010/0243889 | A1 | 9/2010 | Faber et al. |
| 2010/0300873 | A1* | 12/2010 | Blackwood et al. ..... 204/192.33 |
| 2011/0006207 | A1* | 1/2011 | Arjavac et al. ............... 250/307 |

FOREIGN PATENT DOCUMENTS

| | | |
|---|---|---|
| WO | 2008049133 | 4/2008 |
| WO | 2008049134 | 4/2008 |
| WO | 2010051546 A2 | 5/2010 |

OTHER PUBLICATIONS

Coyne, Edward, 'A Working Method for Adapting the (SEM) Scanning Electron Microscope to Produce (STEM) Scanning Transmission Electron Microscope Images,' Proceedings from the 28th International Symposium for Testing and Failure Analysis, Nov. 3-7, 2002, pp. 93-99.

Klein, P., et al., 'New Expressions for Angular Distributions,' Scanning, 1996, pp. 417-427, vol. 18.

Vanderlinde, Willliam, E., 'STEM (Scanning Transmission Electron Microscopy) in a SEM (Scanning Electron Microscope) for Failure Analysis and Metrology,' Proceedings from the 28th International Symposium for Testing and Failure Analysis, Nov. 3-7, 2002, pp. 77-85.

Young, Richard, et al., 'Applications of In-Situ Sample Preparation and Modeling of SEM-STEM Imaging,' ISTFA 2008: Proceedings from the 34th International Symposium for Testing and Failure Analysis, Nov. 2-6, 2008, pp. 320-327.

Young, Richard, et al., 'Dual-Beam (FEIB-SEM) Systems,' Introduction to Focused Ion Beams: Instrumentation, Theory, Techniques, and Practice, 2004, pp. 247-280.

Braun, Artur, 'Carbon Speciation in Airborne Particulate Matter with C (1s) NEXAFS Spectroscopy,' J. Environ Monit., 2005, pp. 1059-1065, vol. 7.

Boyall, N.M. et al., 'A Method of Normalizing Cathodoluminescence Images of Electron Transparent Foils for Thickness Contrast Applied to InGaN Quantum Wells,' Journal of Microscopy, Jan. 2003, pp. 41-46, vol. 209.

Young, Richard J., et al., 'In-Situ Preparation and High-Resolution SEM-STEM Analysis,' 30th International Symposium for Testing and Failure Analysis, Nov. 14-18, 2004, pp. 331-337, Worcester, Massachusetts.

Gnauck, Peter et al., "Application of the CrossBeam Technology to TEM Sample Preparation and Nanolithography," Microscopy and Microanalysis, 2004, 6 pgs, vol. 10, Suppl. 2.

Smith, Steven W., "Brightness and Contrast Adjustments," The Scientist and Engineer's Guide to Digital Signal Processing, 1997, 5 pgs.

Kanaya, K., et al. Penetration and energy-loss theory of electrons in solid targets, Journal of Applied Physics D: Applied Physics, Jan. 1972, pp. 43-58, vol. 5.

* cited by examiner

MEASUREMENT AND ENDPOINTING OF SAMPLE THICKNESS

This application claims priority from U.S. Provisional Pat. App. No. 61/110,394, filed Oct. 31, 2008, which is hereby incorporated by reference.

TECHNICAL FIELD OF THE INVENTION

The present invention relates to preparation of samples and methods of analysis for transmission electron microscopes and scanning transmission electron microscopes.

BACKGROUND OF THE INVENTION

Semiconductor manufacturing, such as the fabrication of integrated circuits, typically entails the use of photolithography. A semiconductor substrate on which circuits are being formed, usually a silicon wafer, is coated with a material, such as a photoresist, that changes solubility when exposed to radiation. A lithography tool, such as a mask or reticle, positioned between the radiation source and the semiconductor substrate casts a shadow to control which areas of the substrate are exposed to the radiation. After the exposure, the photoresist is removed from either the exposed or the unexposed areas, leaving a patterned layer of photoresist on the wafer that protects parts of the wafer during a subsequent etching or diffusion process.

The photolithography process allows multiple integrated circuit devices or electromechanical devices, often referred to as "chips," to be formed on each wafer. The wafer is then cut up into individual dies, each including a single integrated circuit device or electromechanical device. Ultimately, these dies are subjected to additional operations and packaged into individual integrated circuit chips or electromechanical devices.

During the manufacturing process, variations in exposure and focus require that the patterns developed by lithographic processes be continually monitored or measured to determine if the dimensions of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing of interconnecting lines, spacing and diameter of contact holes, and the surface geometry such as corners and edges of various features. Features on the wafer are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and assure a desired device geometry is obtained.

Typically, CD measurements are made using instruments such as a scanning electron microscope (SEM). In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

Transmission electron microscopes (TEMs) allow observers to see extremely small features, on the order of nanometers. In contrast to SEMs, which only image the surface of a material, TEMs also allow analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite side. Samples, also referred to as lamellae, are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface. The term "TEM" as used herein refers to a TEM or a STEM and references to preparing a sample for a TEM are to be understood to also include preparing a sample for viewing on a STEM. The term "S/TEM" as used herein also refers to both TEM and STEM.

Bright field imaging and dark field imaging are often used in the context of STEM imaging. A bright field image may be formed by selecting electrons from a central diffraction spot to form the image. In other words, bright-field images are formed by detecting the electrons that pass through the sample without significantly scattering as they pass through the sample. In contrast, a dark field image may be formed in the STEM by using some or all of the non-central (diffracted) electrons. The dark-field images are obtained by detecting the electrons that scatter as they pass through the sample.

Figure 1A:
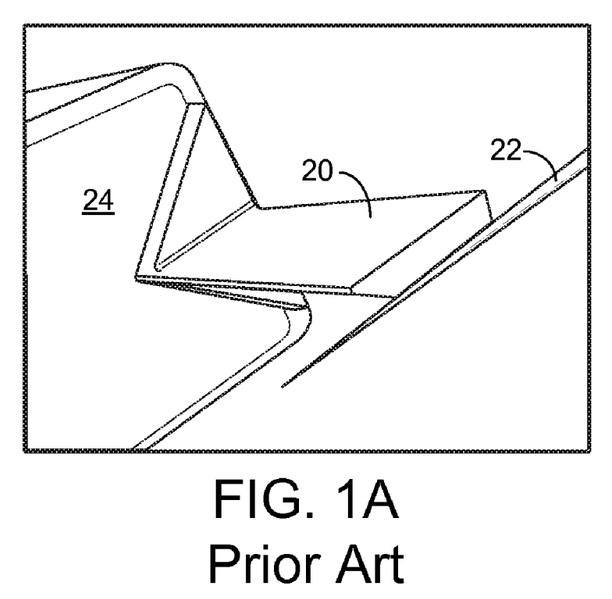
FIG. 1A shows sample thinning using a focused ion beam according to the prior art.
Figure 1B:
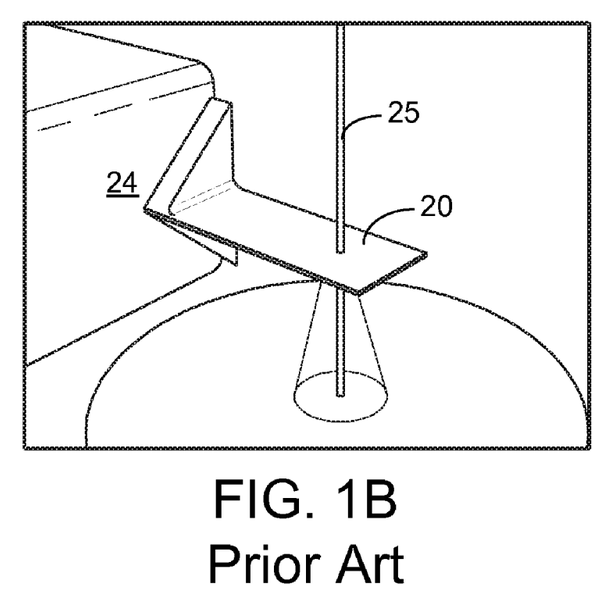
FIG. 1B shows imaging of the thinned sample of FIG. 1A using a S/TEM according to the prior art.

FIGS. 1A and 1B show steps in thinning and imaging a TEM sample according to the prior art. The sample 20 is typically attached to a TEM sample holder 24 and thinned using a focused ion beam 22 (FIB). The sample can be imaged with an electron beam 25 in a TEM or STEM as shown in FIG. 1B. A typical dual beam FIB/SEM has the SEM column oriented normal to the sample (at 90 degrees) and the FIB column at an angle of approximately 52 degrees. It is often desirable to image the sample during milling using the SEM. Imaging using SEM or S/TEM during sample thinning allows the sample thickness and location of the feature of interest within the sample to be monitored directly. S/TEM imaging can be used even when the sample surface is at an angle to the electron beam (as would be the case when the sample is oriented toward the ion beam during milling) by compensating for the angle mathematically.

Because a sample must be very thin for viewing with transmission electron microscopy (whether TEM or STEM), preparation of the sample can be delicate, time-consuming work. Accurately determining the endpoint for lamella creation is becoming even more difficult as devices grow in complexity and shrink in size. Smaller features can require smaller and thinner S/TEM samples. In many cases, samples are thinned using a focused ion beam system. It is often very difficult to determine when the sample has been sufficiently thinned. If samples are left too thick they won't be sufficiently transparent to the electrons for S/TEM analysis. On the other hand, if the sample is thinned too much, the features to be measured or even the entire sample may be destroyed. Even for a sample that is within the acceptable range of thickness, variation between samples is undesirable.

Consequently, precise endpoint detection for lamella thinning is very important. Historically, the TEM sample preparation process has been performed using instruments operated manually. Attempting to determine the precise endpoint for sample thinning (i.e., endpointing) is typically more of a guess than an actual calculated endpoint determination. For this reason, successful S/TEM sample preparation generally requires the use of highly trained and experienced operators and technicians. Even then, it is very difficult to meet any reasonable standards of reproducibility and throughput. Even though the information that can be discovered by TEM analysis can be very valuable, the entire process of creating and measuring TEM samples has historically been so labor intensive and time consuming that it has not been practical to use this type of analysis for manufacturing process control.

What is needed is a method of precisely calculating an endpoint for FIB sample thinning to use in TEM sample creation. What is also needed is a method that lends itself to automation to increase throughput and reproducibility so that TEM measurement can be incorporated into integrated or in situ metrology for process control.

SUMMARY OF THE INVENTION

An object of the invention, therefore, is to provide an improved method for TEM sample creation. Preferred embodiments of the present invention provide improved methods for endpointing sample thinning and methods to partially or fully automate endpointing to increase throughput and reproducibility of TEM sample creation.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Preferred embodiments of the present invention provide improved methods for lamella creation. The use of a SEM-S/TEM detector in the dual-beam FIB/SEM allows a sample to be thinned using the FIB, while the STEM signal is used to monitor sample thickness. By mounting the sample on a pivoting sub-stage (a "flipstage") it is possible to orient the sample for FIB thinning and then to position it for SEM-S/TEM imaging without breaking vacuum, enabling fast inspection of the thinned sample and even direct monitoring of the thinning process. Preferably, the electron beam and the ion beam can be operated at the same time (or intermittently) so thickness measurement is available during the thinning process.

A preferred embodiment of the present invention can measure the thickness of or create S/TEM samples by using a precise endpoint detection method that is reproducible and suitable for automation. Preferred embodiments also enable automatic endpointing during TEM lamella creation and provide users with direct feedback on sample thickness during manual thinning.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable.

Known automatic lamella milling routines are typically limited to rough milling of lamellae which are approximately 250-500 nm thick. Further thinning is typically manually controlled in order to achieve the desired lamella thicknesses of 100 nm or less. Preferred embodiments of the present invention provide an improvement of existing small dual beam (SDB) and wafer tool thinning schemes. Preferred embodiments provide direct feedback relating to sample thickness that is suitable for automatic endpointing of S/TEM lamella creation and also for manually thinning. Prior art methods of lamella thinning using STEM signals have been more of a guess than an actual calculated endpoint determination. By basing the endpoint determination on a real signal value, sample preparation becomes more repeatable. In preferred embodiments, the operator may input a desired thickness for remaining lamella material at endpoint, and the remainder of the process by suitable programming may be entirely automatic.

According to one preferred embodiment of the present invention, an S/TEM bright-field signal can be used to determine a milling endpoint during lamella creation. As described above, the bright-field signal (BF) is produced by the electrons that pass through a sample without significant diffraction. A monotonic relationship links the thickness and transmitted signal, and once this relationship is understood for a particular material, it can be used to this can be used to determine an endpoint for lamella thinning.

Figure 2:
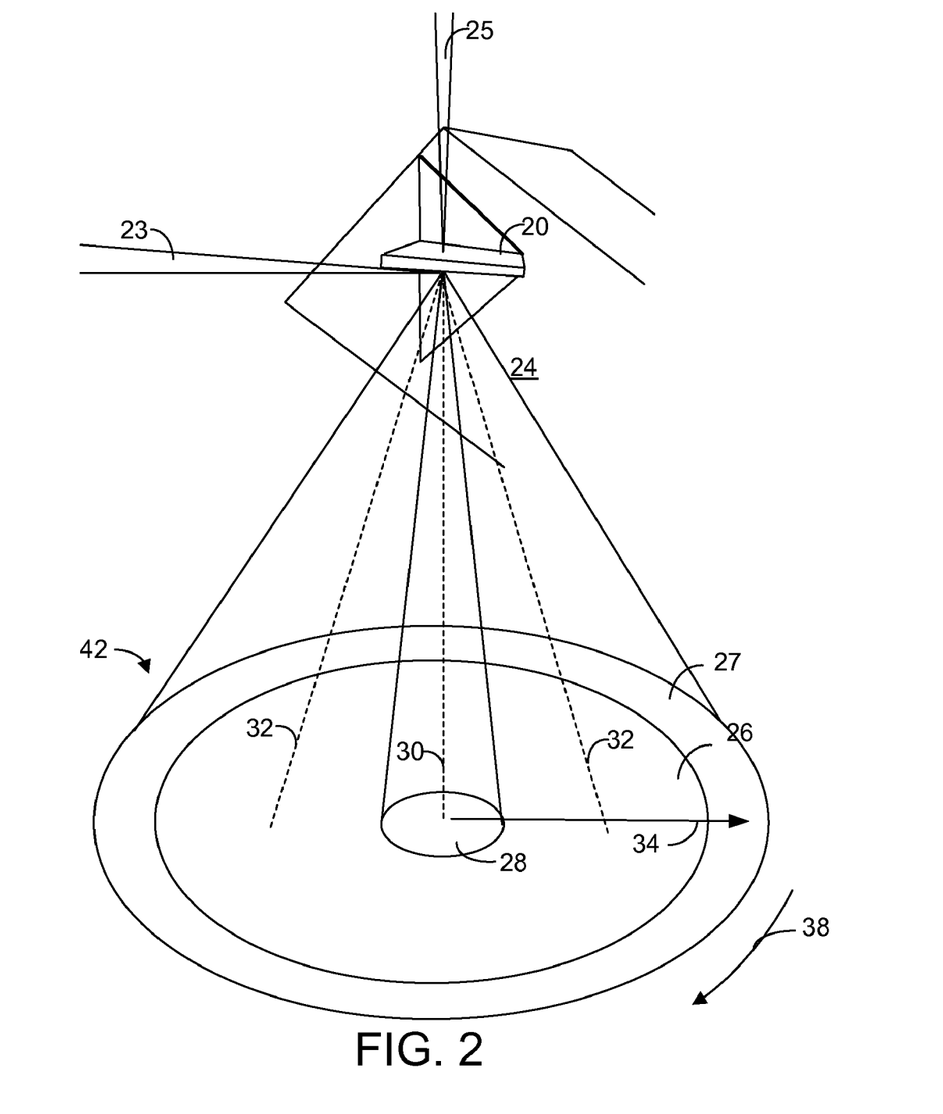
FIG. 2 shows a dual beam FIB/S/TEM with bright-field and dark-field detectors.

An important consideration in preferred embodiments of the present invention is the normalization of the bright-field signal. As shown in FIG. 2, during a scan using a bright-field detector, a primary electron beam 25 is focused to a fine spot that scans the surface of the sample 20 to be observed. The electrons passing through the sample are collected by a TEM detector, either the bright-field portion of the detector 28 or the dark-field portion of the detector (divided into the annular dark field 26 and the high angle dark field 27). Either the bright-field electrons 30 or the dark-field electrons 32 are detected, and an image of the sample is formed, with the brightness at each point of the image being determined by the number of electrons detected when the beam impacts a corresponding spot on the sample surface. According to preferred embodiments of the present invention, the sample can be imaged by the S/TEM during sample thinning with the FIB 23.

Figure 3:
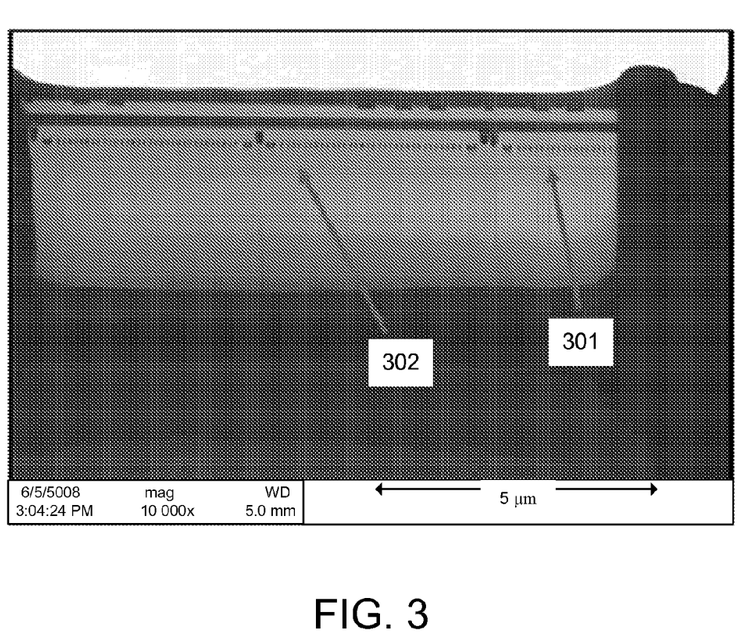
FIG. 3 shows a S/TEM image of a sample.

As the signal is collected, it is converted to an electron microscope image by assigning video "gray levels" to the signal intensity at each point in the scan (commonly referred to as a pixel). Although the gray-level resolution (the number of shades of gray used in the image) can be varied, typically 256 gray levels are used, so that each point is assigned a value from 0 (black) to 255 (white) according to the number of electrons collected by the electron detector while the electron beam was impinging at that point. The value for each pixel is stored in a memory array and used to produce a multilevel gray image of the target surface. Areas where a relatively low number of electrons are detected will appear darker in the image, while areas where a relatively high number of electrons are detected will appear brighter. A typical S/TEM image of a sample is shown in FIG. 3.

The signal itself is subject to certain types of manipulation as it is being collected (or afterwards). For example, on the video display, "brightness" refers to biasing (vertical offset) of a video signal at some level in between the video black and the video white levels. "Contrast" refers to the signal range between the "blackest" value of the signal and the "whitest" value of the signal. For a BF signal, the areas where the transmission of electrons through the sample is highest will appear brighter (whiter), while the areas where transmission is lowest will appear darker. It is common for an operator to adjust the brightness and contrast values as the scanned image is being created in order to improve the sample image.

In a preferred embodiment, the S/TEM BF signal can be "normalized" to provide a more robust thickness measurement and endpoint determination suitable for automation or direct monitoring. A S/TEM scan of the lamella will preferably include areas where the sample or mounting grid (onto which the sample is typically attached) is thick enough that there will be a very low or zero BF signal (for example >500 nm for silicon) because few electrons are passing through the sample. This area (or areas) can be assigned a 0% transmission value. Additionally, the scan should include a location where the beam misses the sample so that all of the electrons reach the BF detector. This area (or areas) can be assigned a 100% transmission value. In terms of the image, the "thick" areas will be the darkest areas in the image and the 100% transmission location will be the brightest. By normalizing the raw signal of the area of interest between the known 0% transmission areas and the 100% areas, it is possible to get a good idea of sample thickness within a single scan, rather than relying on monitoring the trend of a single signal from image to image as in the prior art. The present invention thus allows the use of a single signal image to obtain contrast/thickness information (after calibration) instead of requiring a comparison of multiple sequential images as the sample is thinned.

Further, under the prior art, the detector settings or the beam settings cannot be changed during the thinning process without losing the ability to compare the images and the contrast scaling. By normalizing the signal using the 100% transmission and 0% transmission areas, the thickness of the lamella can be roughly determined by the transmission through the lamella as compared to the 100% and 0% areas. For an initial S/TEM scan, the brightness and contrast values for the S/TEM detector could be set at any arbitrary setting. Assuming the signal is not clipped or off the scale, the lamella thickness can be determined by observing the silicon contrast value within the scale of the 0% signal (or the signals very close to 0%) and the 100% signal. For instance, if a silicon contrast value is ⅔ of the way to 100%, a change in the detector settings (brightness or contrast) or the beam current will not affect the fraction of the silicon contrast in the full scale, even though the actual contrast value itself may change. The use of internal referencing (within the scanned image) helps to insulate the thickness determination from these kinds of detector setting or beam current changes.

Calibrating the STEM apparatus preferably includes matching, or closely approximating, signal efficiency (transmission) to a curve, preferably an idealized curve, representing a motonotic relationship between samples of known thicknesses (and materials) and detected signals. For the best accuracy, two types of calibration are preferred. The first type of calibration can be performed, for example, by the manufacturer of a particular S/TEM system. It is important to take detector geometry, sample spacing, and other factors in a particular S/TEM design into account. Preferably, this is accomplished by way of extensive experimental calibration samples of a particular material of a known thickness using a particular S/TEM design or by some type of computer modeling of the collection efficiency (transmission) and sample thickness for the particular detector of the S/TEM design based on the sample material and on the geometry of the detector and sample spacing. Where the modeling approach is used, even after the modeling gives a good idea of the expected transmission signal change as the sample changes thickness, it is desirable to calibrate the system with at least one real experimental sample of a known thickness. This type of sample modeling is described in greater detail below. Such a contrast/thickness curve (whether developed experimentally or via modeling) can be stored in computer memory, such as in a lookup table or other type of storage.

Figure 4:
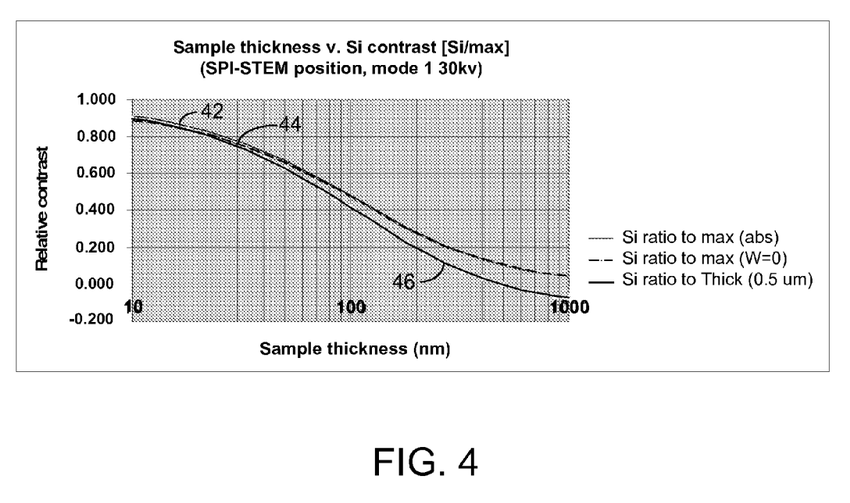
FIG. 4 shows a graph of relative contrast for the bright field (BF) signal against sample thickness with three different normalized curves according to a preferred embodiment of the present invention.

FIG. 4 shows a graph of sample thickness vs. relative contrast for S/TEM BF scans of samples of various thicknesses according to the present invention. Line 42 was normalized using the maximum silicon thickness within the image for 0% transmission; line 44 using a sample section composed of tungsten as 0% transmission; and line 46 represents a signal normalized using a 0.5 µm thick section of silicon as having 0% transmission. Applicants have discovered that a global calibration (i.e., determining the relationship between sample thickness and signal at various signals as shown in FIG. 4) to determine a calibration curve is not required for each different S/TEM system, even though there are unavoidable variations in detector geometry, etc., between all S/TEM systems. Instead, once the global calibration curve for a given material has been developed, a limited local calibration can be quickly performed for the particular S/TEM system in which the samples are being prepared. Calibrating a different S/TEM system only requires one data point (based upon known samples) to fit the curve for a new system to the global calibration curve. Skilled persons will appreciate that multiple data points could be used to increase the accuracy of the calibration. Once the limited calibration is completed, subsequent samples can be measured on a second S/TEM system from a single S/TEM scan. Thus, once the global calibration curve has been created for a given material, subsequent measurements on different samples (on different S/TEM systems) can be easily made by using contrast (transmission) to determine the corresponding sample thickness.

It should be noted that the signal can be normalized over any desired range. For example, a thick section of the silicon substrate (~0.5 μm) could be used as the lower scale value even though there is some limited electron transmission through that region of approximately 5%. In that case (shown by line 46 in FIG. 4) the signal could be normalized from 5% to 100%. As shown in FIG. 4, in that case, the curve after normalization might show a negative transmission for areas with a lower transmission that the section chosen for normalization.

Figure 5A:
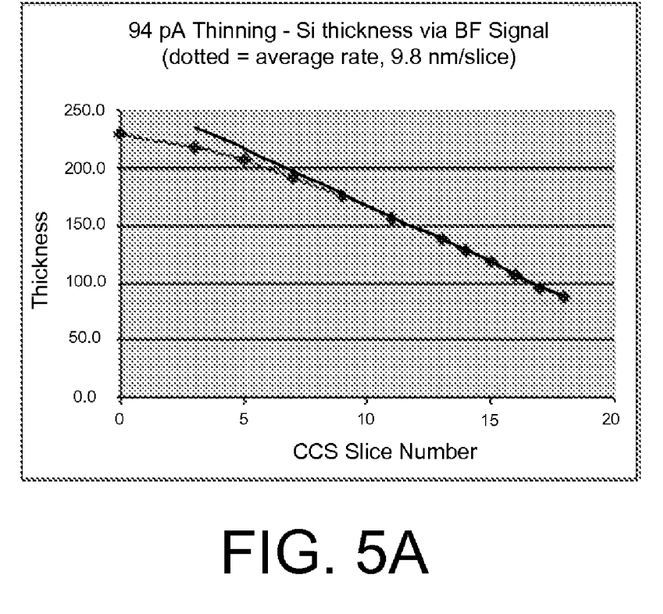
FIGS. 5A-5B show graphs of sample thickness against FIB slice number for two sets of sample thinning.
Figure 5B:
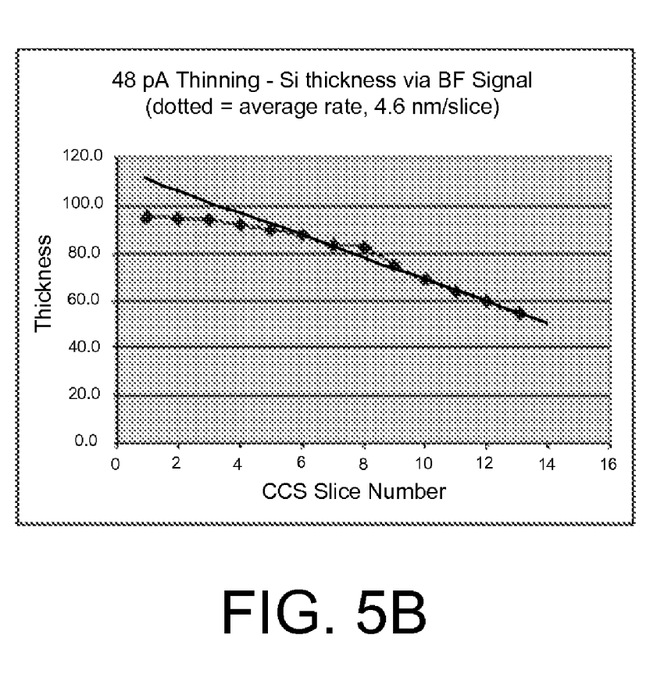

The S/TEM modeling work thus enables a prediction of thickness from a single S/TEM scan or from a number of scans as the thinning process is carried out. FIGS. 5A and 5B show graphs of thickness versus slice number using two different beam currents for the sample thinning (94 pA in FIG. 5A, and 48 pA in FIG. 5B). In preferred embodiments of the present invention, an operator could easily input a desired lamella thickness and have the endpoint determined automatically based upon a particular contrast value. Persons of ordinary skill in the art will appreciate that an actual graphically displayed curve need not be generated for the relationship between contrast values and thickness to be determined (experimentally or by modeling) and for that relationship to be used to determine the thickness (or milling endpoint) for a sample.

Once the appropriate normalized contrast value is established, samples of the same type could be easily and repeatably thinned until the normalized contrast value for the sample equals the desired value (either at a particular predetermined location on the sample or over the entire sample). A computer could readily compare the normalized contrast values for the sample during thinning to the stored data (determined during calibration) and cause the thinning process to stop when the two values match. Further, the contrast value could be set as a minimum (i.e., thinning is stopped when the contrast value at any sample point reaches the stored contrast value) or as a maximum (i.e., thinning is stopped when all contrast values in the sample are less than or equal to the stored contrast value). Other variations could also be used, such as determining average contrast values for a sample or area of a sample. In this fashion, the endpoint determination can be based upon a real signal value and sample preparation becomes more repeatable. In preferred embodiments, the operator may thus input a desired thickness for remaining lamella material at endpoint, and the remainder of the process (including determining the appropriate contrast values from stored data for a given sample material and comparing contrast values during sample thinning to stored data) by suitable programming may be entirely automatic.

In a similar fashion, changes in the S/TEM dark-field signal could also be used to determine thickness for a known material. Depending upon the material, dark field imaging might be more sensitive. As described in greater detail below, the DF signal would not be "normalizable" in the same way as the bright field signal so the measurement process would remain sensitive to changes in detector settings or electron voltage.

In another preferred embodiment of the present invention, an S/TEM dark-field signal can be used to determine a milling endpoint during sample/lamella thinning. As described above, dark-field (DF) images are obtained by detecting the electrons that scatter as they pass through the sample, typically in the annular dark field, but the high angle dark field could also be used. In the bright-field detection embodiment described above, as the sample gets thinner, more electrons pass through the sample and so the signal goes up monotonically. The dark-field signal, however, behaves differently. For a very thick sample, few if any electrons will penetrate the sample so the DF signal will be very low. As the sample is thinned, the DF signal will increase. As the sample begins to get very thin, however, the DF signal will begin to decrease because there is not much sample material to cause scattering of the electrons. More of the electrons will pass straight through the sample to the BF detector rather than being deflected so that they impact the DF detector.

For different materials, the DF signal "peak" will be in different locations. For a mixture of materials, the peaks will be shifted relative to each other. Accordingly, where the DF signal for two different materials are shown on the same graph, there will typically be an intersection point where the two curves crossover. Applicants have discovered that, for a lamella formed from two different materials (such as a silicon wafer with tungsten contacts) the DF signals for the two materials will intersect at a particular sample thickness depending upon the electron voltage.

Figure 6:
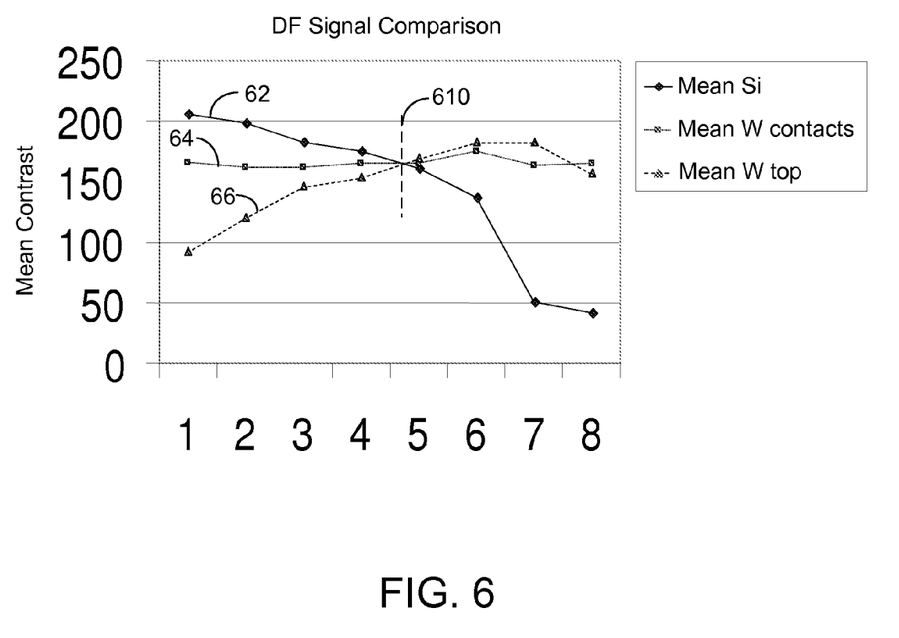
FIG. 6 shows a graph of dark field signal contrast against scan number for three different materials in a sample.

FIG. 6 shows a graph of DF contrast values (at an electron voltage of 30 kV) vs. image number (as the sample is being thinned) for an area of silicon (shown by line 62) and for two different areas composed of tungsten (an overlayer on top if the lamella shown by line 64 and tungsten contacts shown by line 66). Instead of image number, DF contrast values could be graphed against actual sample thickness where known calibration samples are used. As shown in the graph, the curves for Si and W intersect or crossover at point 610, which the modeling predicts to be a sample thickness of ~65 nm. When an unknown sample is incrementally thinned until the crossover point is reached, the precise thickness at the crossover point will need to be determined by other means. The relationship between crossover point and sample thickness can also be easily determined experimentally. As long as the beam voltage is kept constant, this crossover point will always occur at the same sample thickness. As a result, this crossover point can be used as a reliable and repeatable endpoint determination. A Si and W sample can be thinned at 30 kV and when the DF contrast values for Si and W are identical, the sample will be approximately 65 nm in thickness. Significantly, this crossover reference point is independent of source and detector conditions.

Applicants have also discovered that the crossover point will correspond to a different sample thickness at a different electron voltage. Thus, for the curves shown in FIG. 6, if the electron voltage is reduced to 20 kV, the sample thickness at the crossover point might be only 50 nm. For a given combination of materials, the electron voltage required to produce a desired sample thickness could be determined, either experimentally or by modeling (or by a combination of modeling and a limited amount of experimentation). Once the appropriate electron voltage is established, samples of the same type could be easily and repeatably thinned until the DF contrast levels for the different materials are equal. A computer could readily compare contrast values for the two materials (for example, silicon and tungsten) and cause the thinning process to stop when the contrast values for the two material areas match. Because this preferred embodiment is internally referenced to a contrast difference within the STEM images, it is more robust and independent of sample geometry, as compared to prior art methods.

In some preferred embodiments, an electron voltage and a desired sample thickness could be selected by a user and the thinning process could then proceed automatically. Image recognition could be used to automatically select appropriate areas (for example, areas containing silicon or areas containing tungsten) to be scanned and then the sample could be automatically thinned until the contrast levels are equal (and the sample is at the desired thickness).

In another preferred embodiment of the present invention, an SEM backscatter signal can be used to determine a milling endpoint during lamella creation. Using a backscatter signal will result in more signal from thick areas of the sample due to more electron interaction. Thinner areas will produce a lower signal. As a result, the SEM backscatter signal could be normalized using areas with high signal (100%) and very low signal (0%). One difficulty in using the backscatter signal is that it is sometimes difficult to separate true backscattered electrons from secondary electrons. In some embodiments, the SEM secondary electrons or a combination of backscattered and secondary electrons could be used to determine a milling endpoint. There are a number of geometric dependencies, however, that make it difficult to normalize a signal containing secondary electrons.

The increased throughput and reproducibility of the TEM sample thinning and preparation provided by the present invention allows TEM based metrology to be more easily used for in-line process control on objects such as integrated circuits on a semiconductor. For example, S/TEM samples created according to the present invention could be utilized in a wafer fabrication facility to provide rapid feedback to process engineers to troubleshoot or improve processes. This kind of process control for the very small features that can only be measured by S/TEM is not practical using prior art TEM sample preparation methods.

Sample Contrast Modeling

Below are some examples of modeling undertaken to understand better the expected contrasts seen in the various SEM-STEM modes and how they change with imaging conditions, such as, sample thickness, electron beam voltage and different material parameters. Such modeling can help interpret the contrast seen within the SEM-STEM images and help optimize sample preparation and imaging conditions.

SEM-STEM detectors are available for many different types of SEM and dual-beam FIB/SEM instruments, including systems that use full wafers as well as those that handle wafer pieces and packaged parts. Such STEM detectors add the capability for high-contrast, high-resolution imaging at <0.8 nm resolution. The operation of the various STEM detectors is similar, although the sample-detector geometries and signal detection methods vary.

Referring to FIG. 2, the STEM detector 42 is placed some distance below a thin sample 20, enabling transmitted electrons 30, 32 to be detected using, for example, a solid state diode similar to those used in back scatter electron detectors. The detectors are often divided up into a number of separate regions that can each be used alone or with other regions to form the final image. Bright field (BF) images are formed from electrons that exit the sample directly below the incident beam and strike the bright field portion of the detector 28, while dark field images (ADF—annular dark field 26; and HADF—high angle dark field 27) are formed from more scattered electrons. In addition, in the detectors considered here, the HADF region is broken into 12 sub-segments (like a clock-face), enabling collection of signal from either the full annular region, or just a fraction of it (not shown).

The interaction of the beam with the sample results in a series of scattering events and other interactions that produces a transmitted beam with some angular distribution of intensity in both the polar 34 (angle to the incident beam) and azimuthal 38 (angle in the plane of the detector) directions. The azimuthal angular variation mainly comes into play when considering interfaces between materials, but for a uniform amorphous material it can be ignored and only the polar variation considered.

An initial study was carried out using a Monte-Carlo modeling program to simulate how the incoming electrons interacted with various materials and sample thicknesses. The program used for the study is "MC-SET". This program allows the trajectory of the transmitted electrons to be tracked based on data in the log file created. An experiment is set up with a sample of a given thickness and set of materials. The program allows one parameter to be varied to create a series of result files, for example beam position or beam energy.

Each region in a sample is characterized by atomic number (Z), atomic weight (A) and density (D) (g/cm2). This data is normally straightforward for elements, but for compounds there are several methods for how to combine the various A and Z values to give aggregate values for the region. The two main methods to calculate the aggregate A and Z are weighting the values based on number (atomic) fraction or by weight fraction. Which method to use for general Monte Carlo experiments seems to vary by application, and sometimes one is used for Z and one for A. For these tests, the weight fraction method was generally employed. Also, the density value for a compound may not be well known, or could be different from the typical bulk value due to the method of deposition. In addition, the Monte-Carlo modeling treats the material as amorphous, so crystalline effects have not been considered in the current modeling.

For each experiment MC-SET creates a series of data files that include information on electron trajectory through the samples and transmitted and backscattered electrons. The transmitted data files were imported and analyzed by a series of scripts that enables the angle of each electron relative to the incident beam to be calculated. The angular distribution of electrons can then be combined with knowledge of the sample-to-detector spacing and the detector geometry to calculate which part of the detector the electron will hit, and therefore which type of image (BF, ADF, HADF) the electron will contribute to. For some lens conditions, the magnetic immersion field also needs to be taken into account as this will change the effective angle of electrons that are collected by each detector segment.

A histogram of these polar angles in 1 degree increments is the result for each set of conditions. The signal for a particular detector configuration can then be calculated from this histogram by summing up the appropriate angular contributions. It is also possible to calculate the azimuthal angle so that signals into different sectors of a high-angle dark field detector can be considered. This was investigated for a SiO2-TiN-W interface which shows positional contrast on real samples, as described below.

The initial tests were carried out using 4000 electrons per run. Better statistics could be obtained using additional electrons, especially at higher angles where there are generally few electrons scattered, but the overall trends would not be expected to change. Subsequent tests used 50,000 electrons to improve statistics.

Test results show the angular dependency of counts for a 100 nm thick silicon sample over a range of beam voltages. Below approx. 2.25 kV no electrons are transmitted through the sample. The count rate tends to zero at 0° due to the vanishing small area over which the flux is applied. The count rate shows a peak at some angle that increases in angle and decreases in value with reducing beam voltage, with the largest peak angle being approx. 600 mrad (35°) before the beam voltage is so low that no electrons are transmitted through the sample at all.

There are some models for how to consider the angular count rate for transmitted electrons. This model uses a single parameter to describe the overall shape of the count rate with a function: $\exp(-b \cdot \sin(\theta)) \cdot \cos(\theta) \cdot \sin(\theta)$.

Experiments were run on a set of 6 materials using a variety of beam voltages and sample thicknesses for the annular STEM configuration.

Overall, the trends are that the bright field signals get larger as the sample thickness is reduced. The ADF and HADF signals are more complicated with a peak occurring at some thickness for each material. This occurs because when the sample is very thin there is little scattering into the dark field regions and at larger thickness the beam does not make it through the material. The peaks in the ADF signal occur at smaller sample thickness than the HADF, which is to be expected as less scattering is needed for electrons to reach the ADF region.

These results were compared to a typical STEM results for BF, ADF and HADF modes. The exact materials making up the ILD (inter-layer dielectric) are not known, but the contrast is expected to be similar to SiO2. For the three key materials present, similar signal intensity trends were observed, as shown below:

BF (a): ILD>Si>W
ADF (b): Si>ILD>W
HADF (c): W>Si>ILD

When the results above were inspected, it was noted that very similar counts were obtained for certain combinations of beam voltage and thickness. For example, 100 nm @ 30 kV gave the same result (within the statistical variation seen in Monte Carlo) for BF, ADF and HADF as 50 nm @ 20 kV. This was true for each material and for other thickness-kV combinations.

Overall, for a given material the same counts were obtained when (thickness/kV1.7) was constant.

This result is consistent with the maximum range model of Kanaya-Okayama (KO) as demonstrated in K. Kanaya and S. Okayama, "Penetration and energy-loss theory of electrons in solid targets," J. Phys. D: Appl. Phys, 5 (1972), pp. 43-58.

This model states that:

$$\text{Max range, } R_{KO} = 0.0276 \cdot A \cdot E^{1.67}/(D \cdot Z^{0.889})$$

where, E is in kV and range is in μm
The difference between power factors of 1.67 and 1.7 is well within the statistical error of the modeling, so for the later modeling the kV power of 1.67 from KO range was used for consistency.

Some experiments were also carried out with samples tilted into the "STEM while milling" position (tilted by 38° from the top down STEM imaging position). These results were consistent for each material (except for HADF signal for tungsten) with the sample being simply thicker by the amount expected by increasing the thickness by 1/cos(38°).

These two results mean that for a combination of sample thickness, tilt and beam voltage is possible to calculate the equivalent sample thickness at 30 kV (or conversely to calculate the equivalent beam voltage for a fixed sample thickness, such as 100 nm). Once this 30 kV thickness is known, then the corresponding contrast in the various imaging modes can be predicted.

Further inspection of the data also showed that for a particular material-kV-thickness combination it was possible to find a beam voltage for a 100 nm thick silicon sample with a similar set of results. If this equivalence could be generalized for any set of sample-beam conditions it would be possible to predict the angular distribution (and hence detector signals) by just knowing the results for silicon over a range of beam voltages.

The first model used the following factor, F:

$$F = (D^d \cdot Z^z/A^a) * (t/E^{1.67})$$

where, d, z, a are model parameters and t is sample thickness
Then using
FMaterial=FSilicon
for conditions where the angular distribution are the same then it is possible to calculate the equivalent beam voltage E for Si at some standard thickness (in this case 100 nm).

When this model was applied the best parameters to use were found to be:
z=1.0, a=0.5 and d=1.0

It should be noted that for most material $A \sim 2 \cdot Z$ and so the factor is not too sensitive to changes in both z and a together—e.g. changing to z=1.1 and a=0.6 gives similar results.

These gave a reasonable agreement between the Monte Carlo values for the 6 materials and that predicted by using the Monte Carlo results from the calculated equivalent beam voltage for silicon. The place where the fit for the first model discussed above was least good was in the HADF signal for W in the range 200 nm and above, where it was seen that the modeled signal dropped off too rapidly compared to the Monte Carlo data for W. Under these conditions the beam energy for silicon is getting close to the cut off voltage where no electrons are transmitted (i.e. RKO is approaching the 100 nm standard sample thickness). To overcome this, the following factor was used:

$$F = (D^d \cdot Z^z/A^a) * (t/(E-E_0)^{1.67})$$

Where E0 is the beam voltage where t=RKO for the material. This does not change the t and E dependency for a given material (due to the way E0 is dependent upon t), but means that the factor is effectively using the "excess" beam voltage over that needed to get through the sample and have any transmitted electrons at all.

Using this modified factor the fit was better for W over the full thickness range. The parameters that gave the best fit to the data are:
z=1.9, a=1.0 and d=1.0

As noted above it is possible to change z and a in sync and get a similar fit to the experimental data. For example, using z=1.4 and a=0.5 is almost as good as the values finally used. The attraction of using z=1.9, a=1.0, d=1.0 is that these are very similar to the factors in the KO equation with an additional Z factor (0.889+1~1.9), which simplifies the equation to:

$$F = Z/((R_{KO}/t)^{1/1.67} - 1)^{1.67}$$

With this model in place a wider range of sample conditions can be investigated without having to perform further Monte-Carlo modeling.

Table 1 below lists some of the materials investigated. They are arranged in order of increasing value of the parameter [Dd·Zz/Aa], the "DZ/A factor." This factor is a key value in determining the curve shape (although RKO is also a consideration), so other materials could be estimated simply by looking at an already plotted value with a similar DZ/A value.

The relative STEM signal may be modeled against the scattering angle for the materials in Table 1. By summing the angles that correspond to each region of the STEM detector, the contrast within the different detector modes can be predicted.

TABLE 1

DZ/A factors for a variety of materials commonly found in semiconductor samples.

| Material | Elements | Factor |
| --- | --- | --- |
| Low-k Dielectric | SiOC | 5.9 |
| Dielectric | SiCN | 8.3 |
| Oxide | $SiO_2$ | 9.9 |
| Silicon/Poly-Si | Si | 12.5 |
| Nitraide | $Si_3N_4$ | 14.0 |
| Silicon Germanium | SiGe | 23.1 |
| Silicide | NiSi | 44.5 |
| W-Barrier | TiN | 43.6 |
| Copper | Cu | 84.5 |
| Cu-Barrier | TaN | 247.7 |
| Tungsten | W | 373.8 |

Such modeling can help interpret the contrast seen within the SEM-STEM images and help optimize sample preparation and imaging conditions. To compare the modeling to actual STEM images, the regions of different materials in a sample were identified.

In addition to looking at materials in isolation, the simulation of interfaces was also carried out using the Monte-Carlo program. For example, the 100 nm thick sample consisting of a SiO2-TiN—W sandwich, with the TiN layer being 10 nm wide was imaged. The electron beam was scanned in 1 nm steps across this interface (assuming a zero dimension electron beam).

The results matched the modeled images already considered for the cases of bright field and annular dark field—the bright field signal was brighter in the oxide and then dropped off to a low level in the Tungsten; while annular dark field signal had a peak in the TiN film.

The behavior at the interface was more complicated than it would be without the interface present. Now a peak is seen near the interface before the signal levels off approximately 30 nm from the TiN—W interface. By investigating the azimuthal annular distribution of the transmitted signal this peak can be explained. The HADF transmitted signal was considered for the two halves of the detector—the left half of the detector showed a high peak just inside the W layer, while the right half showed much lower signal in this region.

This behavior is attributed to how the scattering occurs within the W layer. Multiple scattering events will occur within the dense W layer and so if any of these result in an electron scattering out of the W and into the TiN/Oxide region then there is a higher probability that it will eventually make its way out of the sample and reach the detector than would be the case of an electron scattering in the opposite direction and had more scattering events in the W layer. Therefore, the half of the HADF on the oxide side of the sample will see increased signal, while the other side sees a reduced one.

In addition to watching features as they are thinned or eliminated from the image, the transmitted signal (image contrast) will change as the sample is thinned in a predictable way based on the detector geometry in use and beam voltage, sample tilt etc. Therefore, by monitoring the transmitted signal thickness can be directly measured via the modeled data.

In addition to direct monitoring of the sample thickness such a method can also show the angle between locations (such as between points 301 and 302 in FIG. 3). Knowing that an included angle (for example 0.3° in FIG. 3) is being created will allow the operator to make a small scan rotation change to the FIB to make the sample more parallel. Similar measurements can also be made in the vertical direction to check for sample uniformity in that direction too.

Figure 7:
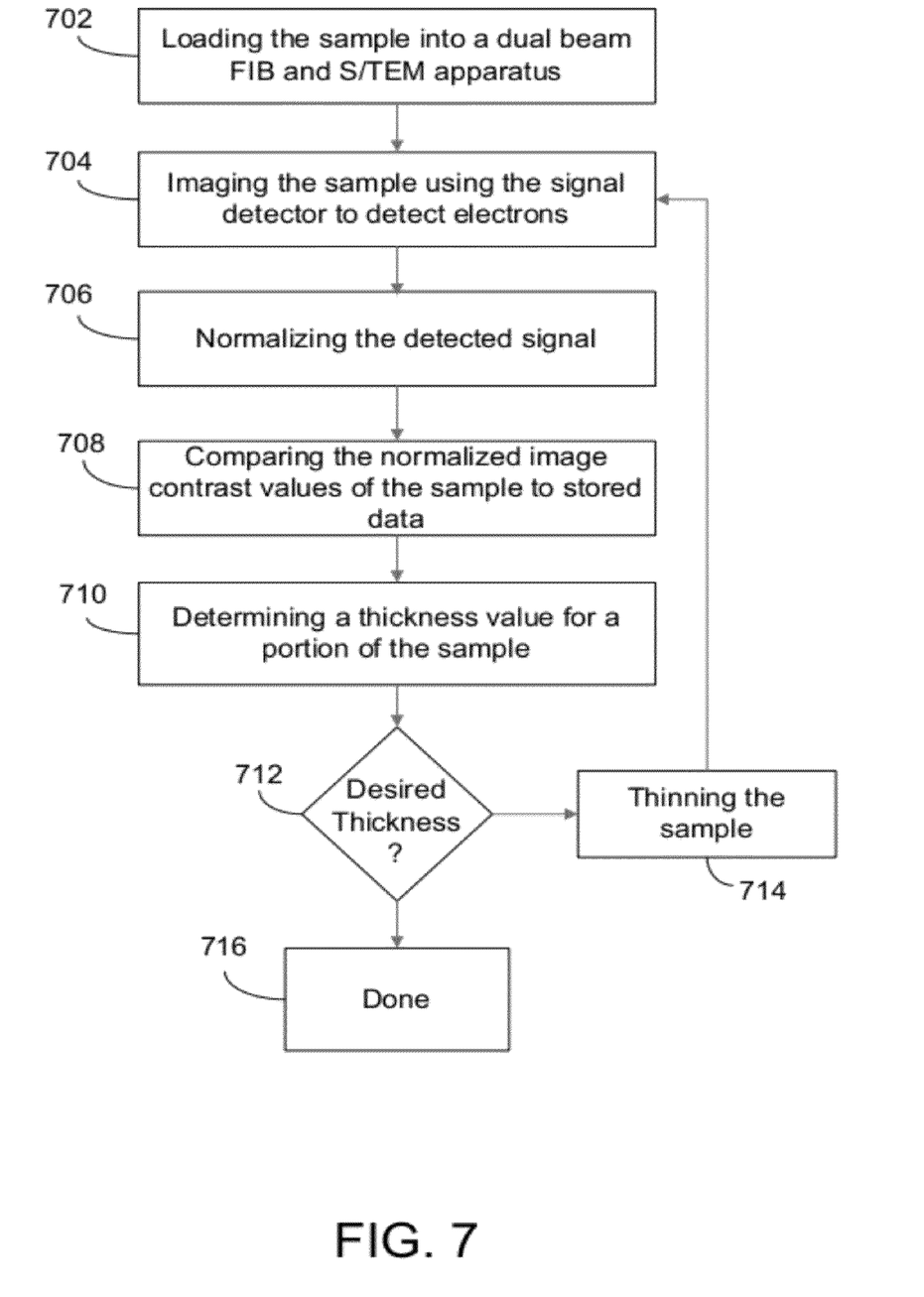
FIG. 7 shows the steps of a method for endpointing the thinning of a sample for S/TEM analysis used in an embodiment of the invention.

FIG. 7 shows the steps of the method for endpointing the thinning of a sample for S/TEM analysis used in an embodiment of the invention. Step 702 includes loading the sample into a dual beam FIB and S/TEM apparatus, the S/TEM comprising an electron column and a signal detector. Step 704 includes imaging the sample using the electron column to direct an electron beam at the sample and using the signal detector to detect electrons passing through the sample. Step 706 includes normalizing the detected signal by assigning a low transmission value to a detected signal in which none or relatively few of the electrons of the beam are detected by the signal detector, and assigning a high transmission value to a detected signal in which substantially all of the electrons of the beam are detected by the signal detector, and normalizing the image contrast values between the low transmission value and the high transmission value. Step 708 includes comparing S/TEM image contrast levels for at least a portion of the sample to stored data. Step 710 includes determining, based upon the relationship between the stored data and the sample contrast values, a thickness value for the at least a portion of the sample. Step 712 is a conditional step that determines if the determined thickness value is greater than a desired thickness value. If the determined thickness is greater than the desired, it will lead to step 714, which includes thinning the sample using FIB milling. Steps 704 through 710 will be repeated until the determined thickness value is equal to the desired thickness value. Once the determined thickness equals the desired thickness value, the process is complete, as shown in step 716.

Figure 8:
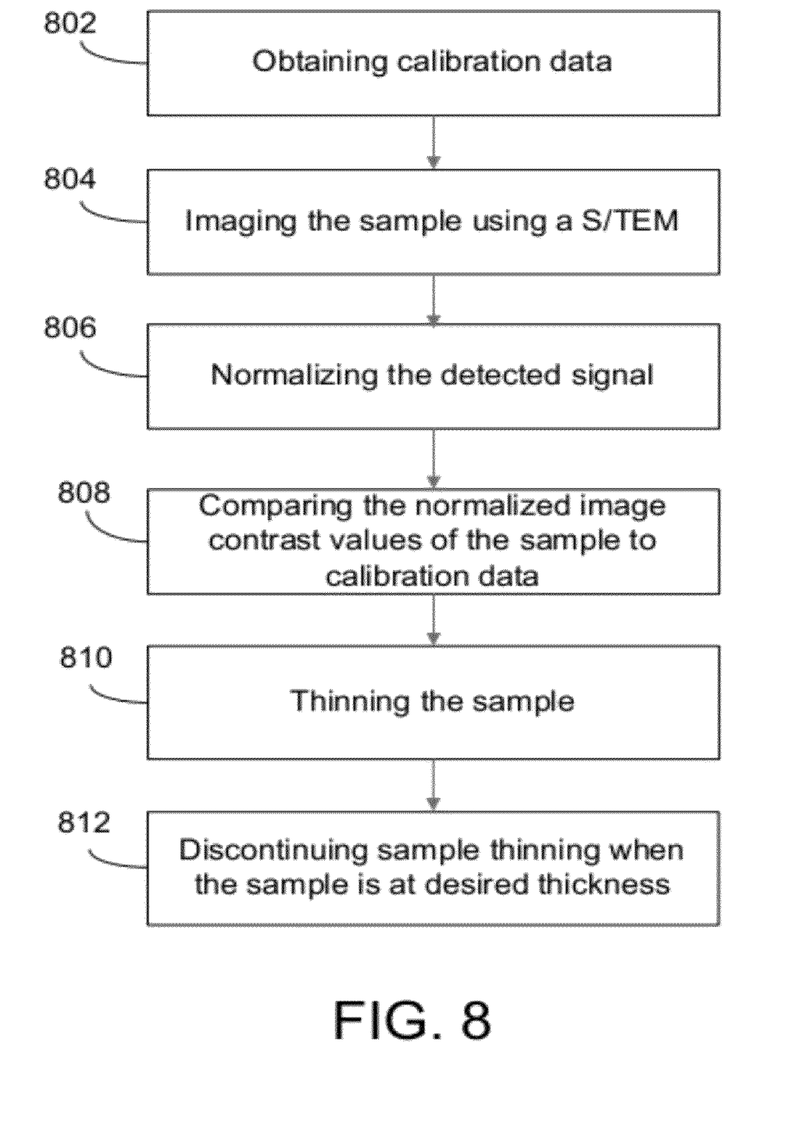
FIG. 8 shows the steps of a method for endpointing the thinning of sample for S/TEM analysis used in another embodiment of the invention.

FIG. 8 shows the steps of a method for endpointing the thinning of sample for S/TEM analysis in another embodiment of the present invention. Step 802 includes obtaining calibration data by determining normalized S/TEM image contrast values for calibration samples of different thicknesses, said calibration samples being of the same material as the sample to be thinned. Step 804 includes imaging the sample using the S/TEM. Step 806 includes normalizing the S/TEM image contrast values for the sample image. Step 808 includes comparing the normalized STEM image contrast values for the sample image to the calibration data. Step 810 includes thinning the sample. Finally, step 812 involves discontinuing sample thinning when the comparison of normalized S/TEM image contrast values for the sample image to the calibration data indicates that the sample is at the desired thickness.

Although the description above is mainly directed at a method for endpointing sample thinning and creation, it should be recognized that an apparatus performing the operation of this method would further be within the scope of the present invention. Further, it should be recognized that embodiments of the present invention can be implemented via computer hardware or software, or a combination of both. The methods can be implemented in computer programs using standard programming techniques—including a computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine readable code, or portions thereof, may be transmitted over a wired or wireless network. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

Preferred embodiments of the present invention have broad applicability and can provide many benefits as described and shown in the examples above. The embodiments will vary greatly depending upon the specific application, and not every embodiment will provide all of the benefits and meet all of the objectives that are achievable by the invention. For example, in a preferred embodiment S/TEM lamella samples are created using a gallium liquid metal ion source to produce a beam of gallium ions focused to a sub-micrometer spot. Such focused ion beam systems are commercially available, for example, from FEI Company, the assignee of the present application. However, even though much of the previous description is directed toward the use of FIB milling, the milling beam used to process the desired S/TEM samples could comprise, for example, an electron beam, a laser beam, or a focused or shaped ion beam, for example, from a liquid metal ion source or a plasma ion source, or any other charged particle beam.

Preferred embodiments of the present invention also make use of a particle beam apparatus, such as a FIB or SEM, in order to image a sample using a beam of particles. Such particles used to image a sample inherently interact with the sample resulting in some degree of physical transformation. Further, throughout the present specification, discussions utilizing terms such as "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

Although much of the previous description is directed at semiconductor wafers, the invention could be applied to any suitable substrate or surface. Also, the present invention is not necessarily limited to S/TEM samples, but could be used for any sample where it is desirable for a sample to be thinned to electron transparency and to have the endpoint determination precisely controlled.

Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . ." The term "integrated circuit" refers to a set of electronic components and their interconnections (internal electrical circuit elements, collectively) that are patterned on the surface of a microchip. The term "semiconductor device" refers generically to an integrated circuit (IC), which may be integral to a semiconductor wafer, singulated from a wafer, or packaged for use on a circuit board. The term "FIB" or "focused ion beam" is used herein to refer to any collimated ion beam, including a beam focused by ion optics and shaped ion beams. To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for endpointing the thinning of a sample for Transmission Electron Microscope or Scanning Transmission Electron Microscope analysis comprising:
   (a) loading the sample into a dual beam focused ion beam and Transmission Electron Microscope or Scanning Transmission Electron Microscope apparatus, the Transmission Electron Microscope or Scanning Transmission Electron Microscope apparatus comprising an electron column and a signal detector;
   (b) imaging the sample using the electron column to direct an electron beam at the sample and using the signal detector to detect electrons passing through the sample;
   (c) normalizing the detected signal by assigning a low transmission value to a detected signal in which none or relatively few of the electrons of the beam are detected by the signal detector, and assigning a high transmission value to a detected signal in which substantially all of the electrons of the beam are detected by the signal detector, and normalizing image contrast values between the low transmission value and the high transmission value;
   (d) comparing the normalized image contrast values for at least a portion of the sample to stored contrast data;

(e) determining, based upon the comparison between the stored contrast data and the image contrast values, a thickness value for the at least a portion of the sample;

(f) if the determined thickness value is greater than a desired thickness value for the sample, thinning the sample using focused ion beam milling;

(g) repeating steps (b) through (e) until the determined thickness value is equal to the desired thickness value, thereby determining the end point of the thinning process.

2. The method of claim 1 in which the stored contrast data comprises stored calibration data showing the relationship for calibration samples between image contrast levels and sample thickness.

3. The method of claim 1 in which the stored data comprises data points of a calibration curve of contrast data versus sample thickness for calibration samples of the same material.

4. The method of claim 1 in which the stored data comprises a stored calibration matching signal transmission for the detected signal through the sample to an idealized curve of known sample thicknesses versus detected signal transmission for the sample material.

5. The method of claim 1 in which the stored data is determined experimentally by Transmission Electron Microscope or Scanning Transmission Electron Microscope imaging of multiple calibration samples having known thicknesses made from the sample material.

6. The method of claim 1 in which the stored data is determined by computer modeling.

7. The method of claim 1 in which the stored data is determined by computer modeling of Transmission Electron Microscope or Scanning Transmission Electron Microscope transmission and sample thickness based on the sample material and on the geometry of the signal detector.

8. The method of claim 1 in which the stored data is determined on a first Transmission Electron Microscope or Scanning Transmission Electron Microscope system and the sample being thinned is imaged using a second Transmission Electron Microscope or Scanning Transmission Electron Microscope system, the method further comprising prior to thinning the sample, determining image contrast levels on the second Transmission Electron Microscope or Scanning Transmission Electron Microscope system for a calibration sample of the same sample material and having a known thickness; and using the image contrast levels for the calibration sample on the second Transmission Electron Microscope or Scanning Transmission Electron Microscope system to match a calibration curve for the second Transmission Electron Microscope or Scanning Transmission Electron Microscope system to the stored data determined on the first Transmission Electron Microscope or Scanning Transmission Electron Microscope system.

9. The method of claim 1 in which imaging the sample comprises imaging the sample using bright field imaging.

10. The method of claim 1, further comprising calibrating the dual beam apparatus to match signal efficiency to a calibration curve.

11. The method of claim 10, in which the calibration curve is specific to a particular dual beam design.

12. The method of claim 10, in which calibrating the dual beam apparatus includes acquiring one or more data points to fit the data points to the calibration curve.

13. The method of claim 1, in which assigning a low transmission value is performed by scanning the electron beam over one or more areas of the sample which are thick enough to prevent all or nearly all of the electrons from reaching the signal detector; and in which assigning a high transmission value is performed by scanning the electron beam over one or more areas of the sample which are thin enough to allow all or nearly all of the electrons to reach the signal detector.

14. The method of claim 13, in which assigning a low transmission value includes assigning a value of between, and including, 0-5%; and in which assigning a high transmission value includes assigning a value of 95-100%.

15. The method of claim 13, in which assigning a low transmission value includes assigning a value of 0%; and in which assigning a high transmission value includes assigning a value of 100%.

16. The method of claim 1, in which the normalized image contrast value remains unchanged as the signal detector and the Scanning Transmission Electron Microscope and Transmission Electron Microscope apparatus settings are changed.

17. The method of claim 16, in which the signal detector and the Scanning Electron Microscope and Transmission Electron Microscope apparatus settings are selected from the group consisting of working distance, sample spacing, beam voltage, detector geometry, sample tilt angle, brightness and contrast.

18. The method of claim 1, further comprising:

inputting, by a user into a machine executing code, a desired sample thickness to be milled by the focused ion beam;

thinning the sample by focused ion beam milling; and ceasing milling upon the determination that the desired sample thickness has been reached.

19. The method of claim 18, in which the step of ceasing milling is initiated by the machine executing computer readable code in communication with the dual beam apparatus.

20. The method of claim 18, in which the step of ceasing milling is performed automatically by the machine executing computer readable code and without user intervention.

21. The method of claim 1 in which normalizing the detected signal, comparing the image contrast values for at least a portion of the sample to stored data, determining a thickness value for the at least a portion of the sample, and/or thinning the sample using focused ion beam milling is done automatically.

22. A method for endpointing the thinning of sample for Transmission Electron Microscope or Scanning Transmission Electron Microscope analysis comprising:

obtaining calibration data by determining normalized image contrast values for calibration samples of different thicknesses, said calibration samples being of the same material as the sample to be thinned;

imaging the sample using the Transmission Electron Microscope or Scanning Transmission Electron Microscope, said Transmission Electron Microscope or Scanning Transmission Electron Microscope comprising an electron column to direct an electron beam at the sample and a signal detector to detect electrons passing though the sample;

normalizing the image contrast values for the sample image;

comparing the normalized image contrast values for the sample image to the calibration data;

thinning the sample; and discontinuing sample thinning when the comparison of normalized image contrast values for the sample image to the calibration data indicates that the sample is at the desired thickness.

23. The method of claim 22 wherein determining normalized image contrast values for calibration samples of different thicknesses comprises assigning a low transmission value to a detected signal in which none or relatively few of the electrons of the beam are detected by the signal detector, assigning a high transmission value to a detected signal in which substantially all of the electrons of the beam are detected by the signal detector, and normalizing the contrast values for the calibration sample images between the low transmission value and the high transmission value.

24. The method of claim 23 in which the low transmission value is 0% and the high transmission value is 100%.

25. The method of claim 22 wherein normalizing the image contrast values for the sample image comprises assigning a low transmission value to a detected signal in which none or relatively few of the electrons of the beam are detected by the signal detector, assigning a high transmission value to a detected signal in which substantially all of the electrons of the beam are detected by the signal detector, and normalizing the contrast values for the sample image between the low transmission value and the high transmission value.

26. The method of claim 25 in which the low transmission value is 0% and the high transmission value is 100%.

27. An apparatus for thinning a sample for Transmission Electron Microscope or Scanning Transmission Electron Microscope analysis comprising:
   a Transmission Electron Microscope or Scanning Transmission Electron Microscope apparatus to image the sample, the Transmission Electron Microscope or Scanning Transmission Electron Microscope including an electron column and a signal detector;
   a focused ion beam column to direct a focused ion beam toward the sample for thinning;
   and
   a computer-readable memory storing calibration data for a sample material, the stored calibration data comprising image contrast values corresponding to sample thicknesses for the sample material for comparing to sample measurement from the Transmission Electron Microscope or Scanning Transmission Electron Microscope to determine when thinning of the sample is complete.

28. The apparatus of claim 27 further comprising a controller to control the focused ion beam to thin the sample to a desired thickness based upon a comparison of the image contrast value for the sample to the stored calibration data.

29. A method for endpointing the thinning of a sample comprised of a mixture of a first material and a second material, the method comprising:
   obtaining calibration data by determining imaging contrast values for the dark field signal crossover point for the first and second sample materials at different electron beam voltages for calibration samples of different thicknesses, said calibration samples being of the same mixture of a first material and a second material as the sample to be thinned;
   selecting a desired electron beam voltage and determining the contrast value for the dark field signal crossover point for that electron beam voltage;
   imaging the sample at the desired electron beam voltage using a Transmission Electron Microscope or Scanning Transmission Electron Microscope to determine the dark field signal for the sample;
   thinning the sample; and
   discontinuing sample thinning when the contrast values for the first and second material of the sample match the dark field crossover point for the calibration sample at a desired thickness.

30. The method of claim 29 wherein determining the imaging contrast values for the dark field signal crossover point comprises obtaining a curve of dark field signal contrast values versus sample thickness for the first and second materials of the sample and determining the sample thickness at which the contrast values for the first and second materials are equal.

* * * * *